(12) United States Patent
Dorogi et al.

(10) Patent No.: US 8,303,984 B2
(45) Date of Patent: Nov. 6, 2012

(54) SKIN TREATMENT COMPOSITIONS CONTAINING COPPER-PIGMENT COMPLEXES

(75) Inventors: Peter Ladislaus Dorogi, Easton, PA (US); David Bruce Vasily, Bethlehem, PA (US); John Patrick McCook, Frisco, TX (US)

(73) Assignee: Discovery Partners, LLC, Frisco, TX (US)

( * ) Notice: Subject to any disclaimer, the term of this patent is extended or adjusted under 35 U.S.C. 154(b) by 50 days.

(21) Appl. No.: 12/796,859

(22) Filed: Jun. 9, 2010

(65) Prior Publication Data

US 2010/0247628 A1    Sep. 30, 2010

Related U.S. Application Data

(63) Continuation of application No. 11/496,151, filed on Jul. 31, 2006, now abandoned, which is a continuation-in-part of application No. 11/320,280, filed on Dec. 28, 2005.

(51) Int. Cl.
*A61K 9/127*     (2006.01)

(52) U.S. Cl. ........................................... 424/450

(58) Field of Classification Search ............... 424/450
See application file for complete search history.

(56) References Cited

U.S. PATENT DOCUMENTS

| 2003/0004499 A1* | 1/2003 | McDaniel | 606/3 |
| 2004/0018237 A1* | 1/2004 | Perricone | 424/484 |
| 2005/0261750 A1* | 11/2005 | McDaniel | 607/86 |
| 2006/0110439 A1* | 5/2006 | Tobia et al. | 424/450 |

OTHER PUBLICATIONS

Touitou, E., et al in Journal of Pharmaceutical Sciences, vol. 83, No. 9, Sep. 1994, pp. 1189-1203.*

* cited by examiner

*Primary Examiner* — Gollamudi Kishore
(74) *Attorney, Agent, or Firm* — Louis C. Paul

(57) ABSTRACT

This invention discloses compositions and method for treating various types of skin disorders, based on topical cutaneous delivery of copper chemically bound with botanical pigments. Sodium-copper-chlorophyllin is used as an example, showing benefits in the treatment of rosacea, acne, oily skin, enlarged pores, and in relieving skin inflammation. Benefits are also disclosed in treatment of environmentally caused premature skin aging, via reductions in fine facial lines and wrinkles, increased tensile strength of the skin, and increased protection against sunlight via increased production of melanin. Therapeutic outcomes are improved when the copper-pigment complex is enclosed within submicron liposomes.

3 Claims, No Drawings

SKIN TREATMENT COMPOSITIONS CONTAINING COPPER-PIGMENT COMPLEXES

This application is a continuation of U.S. application Ser. No. 11/496,151 filed Jul. 31, 2006 now abandoned and titled "Skin Treatment Compositions Containing Copper-Pigment Complexes", which is a continuation-in-part of divisional application Ser. No. 11/320,280 filed Dec. 28, 2005 and titled "SKIN TREATMENT COMPOSITIONS CONTAINING COPPER-PIGMENT COMPLEXES". The disclosures of each of the above-mentioned applications are incorporated herein by reference in their entirety.

This Continuation-in-Part differs from the original application in that the inventors have demonstrated increased utility for the invention, particularly in the treatment of rosacea characterized by diffuse facial redness, with currently no effective topical therapy. The inventors have conducted further experiments to show that artificial light therapy used to treat acne, rosacea, and other inflammatory skin conditions is unnecessary in conjunction with the application of the subject invention, and, is, in fact, contraindicated. Lastly, this Continuation-in-Part more fully describes the formulation options for effective skin penetration of the active copper pigment complex and the effective pH for formulation stability and dermal and epidermal efficacy. The details of the testing related to these new findings and greater utility are described below.

FIELD OF THE INVENTION

This invention relates to therapeutic substances and methods for treating, preventing, reversing or inhibiting skin disorders characterized by redness and broken small blood vessels on the face, associated with, but not limited to rosacea, as well as skin disorders with chronic inflammation or sun damage, by topical application of compositions containing copper bound to a botanical pigment and delivered in a suitable pharmaceutical or cosmeceutical vehicle.

BACKGROUND OF THE INVENTION

Rosacea is typically seen on the face, and is characterized by persistent erythema and broken small blood vessels (telangiectasia). In some cases there are red spots (papules) and sometimes pustules with an acne-like appearance; but in rosacea they are dome-shaped rather than pointed and there are no blackheads, whiteheads, deep cysts, or lumps. The broken blood vessels near the skin surface may leak when flushing or blushing occurs, creating blotchy red areas on the face. The redness can come and go, and the skin may eventually become tender, inflamed and sensitive to the touch. The skin may swell and thicken, and the redness can become permanent. Rosacea is seen mainly in fair-skinned people between 30 and 50 years of age. It is estimated that about 13 million Americans have rosacea.

In individuals who are genetically predisposed to rosacea, the triggering cause is believed to be sun damage to small blood vessels near the skin surface, allowing these vessels to stretch and become permanently dilated by recurrent flushing or blushing. The broken blood vessels may thereafter become visible through the skin surface. Anything that makes such an individual flush or blush promotes rosacea, including consumption of alcohol or spicy foods, heating of the skin, and emotional situations such as anxiety or embarrassment.

Another suspected cause of rosacea is sensitivity to the microbial organism *Demodex folliculorum* (especially in papulopustular rosacea), a relatively common skin parasite. Diffuse skin redness may be due to sympathetic (neural) vasomotor instability, leading to frequent involuntary dilation of the subcutaneous arteries. Therefore, treatment modalities that constrict blood vessels and reduce blood flow have been reported to reduce the diffuse skin redness associated with rosacea, i.e., with erythematotelangiectatic rosacea. The compositions and methods that comprise this invention were found to be effective for the treatment of erythematotelangiectatic rosacea but not papulopustular rosacea. The term "rosacea" used throughout this document refers to the erythematotelangiectatic form of the condition only.

Treatments that strengthen the connective tissue can help by preventing break down of blood vessels. Copper is essential for the maintenance and repair of connective tissue. As a functional component of the enzyme lysyl oxidase, copper catalyzes the formation of structural cross-links in collagen. Damage by environmental factors such as sunlight, pollutants from industrial combustion reactions, and even second-hand cigarette smoke, is prevented by the skin's antioxidant enzymes, most notably the superoxide dismutases (SODs). The predominant form of SOD contains copper. SOD enzymes also neutralize free radical oxidation reactions that underlie the signs and symptoms of rosacea, acne, sunburn, and numerous inflammatory skin pathologies.

Copper is an essential component of the enzyme tyrosine hydroxylase, which catalyzes conversion of the amino acid tyrosine into melanin. With respect to rosacea, tyrosine hydroxylase is also involved in synthesis of the hormone norepinephrine, the natural agonist for activating the alpha-adrenergic receptors responsible for vasoconstriction (reduction of blood flow) in the skin. In prior art, published U.S. Patent Application #20050020600 describes topical application of pharmaceutical preparations containing alpha-adrenergic agonists for the treatment of facial vasomotor instability. This approach differs fundamentally from the present invention, wherein we apply copper to the skin in order to increase the biosynthesis of norepinephrine; but no final agonist is contained in our compositions.

Copper provides two routes for treatment of acne. For one, copper binds to, and activates, certain small peptides that promote wound healing. An example is the tripeptide known by the acronym GHK (glycyl-L-histidyl-L-lysine), which promotes the deposition of new collagen by dermal fibroblasts, stimulating the growth of new blood vessels, and increasing activity of protease enzymes to remove previously formed scar tissue. Copper also has anti-microbial properties and will kill acne-promoting bacteria in the skin, as demonstrated below.

SUMMARY OF THE INVENTION

In the present invention, cutaneous topical delivery of copper is carried out by binding copper with a botanical pigment. The term "pigment" is meant here and throughout this document to cover botanical or naturally-derived chromophoric molecules, or chemically modified botanical chromophores, possessing antioxidant properties. The copper-pigment complex utilized and demonstrated here, in a non-limiting way, is sodium-copper-chlorophyllin. The copper-pigment complex is delivered into the skin with a penetration-enhancing vehicle.

To further improve skin penetration, the copper-pigment complex and its medium may be encapsulated within liposomes. The lipid wall of the liposomes consists of lecithin and is disclosed to have additional advantages if it contains linoleic acid, reported to be therapeutic for acne. The liposomes used are relatively small, with diameters ranging between 150 and 350 nanometers. Sodium-copper-chlorophyllin loaded liposomes are mentioned in U.S. Pat. No. 6,663,559: "Method and apparatus for the photomodulation of living cells". However, this prior art patent is concerned with the use of sodium-copper-chlorophyllin as a chromophore in light radiation treatments of the skin. The present invention does not involve the use of any light sources. In fact, the resulting increase in skin temperature may worsen rosacea.

In summary:

The invention disclosed here is designed, in part, to deliver copper to binding sites in the skin, where it can be utilized to form enzymes and wound-healing copper-peptides; for example, for preventing, reducing and eliminating the signs and symptoms of rosacea.

It is another aim of this invention to provide copper to binding sites where it is utilized to restructure the skin so as to reduce enlarged facial pores (follicular hypertrophy) and the signs and symptoms of acne, notably acne-scarring.

Copper is anti-microbial, and the processes and compositions disclosed in this invention can be used to deliver copper into follicles and sebaceous glands, thereby reducing inflammatory acne by the killing action of copper on the acne-associated bacterium *Propionibacterium acnes*.

The present invention aims to provide copper to copper-dependent antioxidant enzymes responsible for elimination of free radicals generated in the skin by ultraviolet light, reactive oxygen forms, and microbe activity.

The disclosed method is intended to support copper-binding enzymes and peptides which are active in repair and replacement of damaged connective tissue.

It is a further goal of this invention to improve the skin's tanning response to ultraviolet light by providing essential copper to activate the enzyme tyrosine hydroxylase for increased biosynthesis of melanin.

It is also the aim of this invention to simultaneously supply to the skin, besides copper, botanical pigments which are natural antioxidants, so as to further reduce oxidation damage.

We disclose that these goals are achievable with therapeutic units that consist of a copper ion metallically bound to a suitable botanical pigment. Treatment involves cutaneous application of such a copper-pigment complex, delivered in a pharmaceutical or cosmeceutical vehicle that facilitates penetration of the complex into the skin. In one embodiment of the invention, the copper-pigment complex is sodium-copper-chlorophyllin. The copper-pigment complex and its carrier may be encapsulated in 150-350 nanometer diameter liposomes, which are disclosed here to result in increased skin penetration by the copper-pigment complex.

It is understood that in therapeutic applications the composition containing the copper-pigment complex may be combined with or applied in conjunction with other pharmaceutical, cosmeceutical, or nutritional treatments for rosacea, acne, oily skin, enlarged pores, acne scarring, blotchy skin, facial lines and wrinkles or other manifestations of photodamage. Topical application of the copper pigment complex may be sequential or simultaneous with other topical or even systemic treatments, e.g., via injection, inhalation, or ingestion. For example, simultaneous delivery of the copper pigment complex and another pharmaceutical preparation may be accomplished by using a co-dispensing applicator.

It is disclosed here that combining the compositions and processes utilizing copper-pigments with currently established anti-aging, anti-acne, and rosacea treatment technologies will bring additional benefits to those technologies. For example, the anti-inflammatory activity and the control of high skin oil production seen in our studies with sodium-copper-chlorophyllin could be important additions to established treatments. In the acne area, copper-pigment technology could be combined with one or more other treatment compounds that include salicylic acid, retinoids, benzoyl peroxide, azelaic acid, tetracyclines, clindamycin, erythromycin, adapalene, tazarotene, resorcinol, colloidal sulfur, alpha-hydroxy acids or other established anti-acne actives. In the anti-aging area, combinations with one or more compounds that include alpha- and beta-hydroxy acids, peptides, alpha- and beta-keto acids, other antioxidants, sunscreens, isoflavones, metalloprotease enzyme inhibitors or other established anti-aging actives may be advantageous. In the treatment of rosacea, copper-pigment technology may be combined with one or more other treatment compounds that include topical metronidazole, or oral therapy with doxycyline, tetracycline, erythromycin, minocycline, or other established rosacea treatment actives. Co-dispensing the copper-pigment preparation with other actives formulated at an acidic pH could also speed the release of the copper, which may also prove advantageous in some cases.

DETAILED DESCRIPTION OF THE INVENTION

Damaged collagen and elastin can reduce the tensile strength of connective tissue. Structural weakness of connective tissue is a likely cause of telangiectasias, produced by distension and thinning of blood vessel walls. The increased tissue blood volume visible through the skin surface is responsible for the diffuse redness. It is disclosed here that increased cross-linking of connective tissue due to increased bioavailability of copper can 1) reduce the signs and symptoms of rosacea, 2) reduce the visibility of under-eye dark circles, 3) improve tensile strength and elasticity of skin and thereby diminish the appearance of fine lines and wrinkles, and 4) reduce the size of enlarged facial pores.

It is further disclosed that binding copper with an antioxidant botanical pigment provides important additional protection. The skin has its intrinsic mechanisms for repair of damaged cells and macromolecules reduced after oxidative injury. Wound healing may also include the body's own production and secretion of superoxide radicals ($O_2^-$) by phagocytic cells, used to destroy invading microorganisms. Although the superoxide radical is of itself not very damaging, it can react with transition metals such as ferrous iron ($Fe^{+2}$) and cuprous copper ($Cu^{+2}$) to generate the extremely reactive hydroxyl radical $OH^-$. To offset such potentially harmful side-effects, we disclose copper-delivery compositions wherein copper is applied in forms that provide their own antioxidant protection; namely, copper bound with suitable botanical pigments.

Elimination of the superoxides is carried out by superoxide dismutases (SODs). The predominant form of SOD in the skin is the $Cu^{+2}/Zn^{+2-}$ containing dimeric form of the enzyme. It is disclosed here that increasing the amount of copper in the skin may result in increased SOD activity, reducing the signs and symptoms of skin inflammation.

Seborrheic inflammatory conditions may cause excess oiliness of the skin, resulting in a cosmetically unattractive shiny appearance. The anti-inflammatory effect of increased SOD and introduction of the skin-penetrating botanical antioxidant, may account for the reduction in facial skin oiliness observed in the clinical study described below.

The copper-pigment complex is applied to the skin in a pharmaceutical or cosmeceutical vehicle, containing penetration-enhancing ingredients. Non-limiting examples of these ingredients include propylene glycol, butylene glycol, pentylene glycol, isopentyl glycol, ethoxydiglycol, dimethyl isosorbide, acetamide MEA, tetrahydropiperine, various PEG glyceryl ethers, Levomenol [(−)-6-Methyl-2-((4-methyl-3-cyclohexen-1-yl)-5-hepten-2-ol], N-Methyl-2-pyrrolidone, dimethyl sulfoxide and methyl sulfone.

The copper-antioxidant complex and its aqueous vehicle may be delivered within a liposomal dispersion, wherein the lipid shell of the liposome consists of lecithin. Although lecithin has been used for similar applications, the role of lecithin has been viewed strictly as an encapsulating material that facilitates the penetration of hydrophilic substances into the skin. The present invention discloses that if the type of lecithin used is a structural combination of linoleic acid and phosphatidyl choline (high linoleic acid content lecithin), then the liposome material itself may reduce acne symptoms. Liposomes composed of this lipid and loaded with sodium-copper-chlorophyllin were manufactured for us by Rovi Cosmetics (ROVI GmbH & Co., Kosmetische Rohstoffe KG, Schluchtern, Germany). Liposomes of this type can also be made in situ in a suitable cosmetic or pharmaceutical vehicle by dissolving the copper-pigment complex in water and encapsulating the aqueous copper complex with Phospholipon 80® or Phospholipon 85G®. Lecithin of this type was obtained from the American Lecithin Company, originally manufactured by Phospholipid GmbH (Cologne, Germany) and typically contains more than 50% linoleic acid. The copper-complex loaded liposomes are disclosed as novel treatments of rosacea, acne, and other inflammatory skin pathologies. The invention combines four types of ingredients: copper ions, antioxidant botanical pigments, skin penetration enhancing vehicles, and therapeutic lipids in the form of liposomes.

Another aspect of the invention is a method for controlled release of copper in the skin, based on suitable formulation of the pH of the therapeutic unit compared with the internal pH of the skin. In the case of sodium-copper-chlorophyllin, copper is bound to the chlorophyllin by a metallic bond and can be replaced by two protons: a more acidic environment releases the copper, increasing the concentration of the free form, $Cu^{+2}$. It is thereby another aspect of the invention that the therapeutic unit is formulated in a vehicle at a slightly alkaline pH: typically, a pH range of 7.2 to 7.6 gives good results. Aqueous solutions of sodium-copper-chlorophyllin complex are typically alkaline, in the pH-range 8.0-9.5 prior to any pH adjustment via acidifying agents or buffering agents. When liposomal dispersants are used to enhance skin penetration, the pH of the liposomal dispersion is adjusted to a slightly alkaline pH of 7.2-7.6 to stabilize sodium-copper-chlorophyllin.

The more acidic environment of the skin's outer mantle releases copper from the pigment. Encapsulation by liposomes acts as a shield against this "acid shock", resulting in deeper skin penetration, slower release, and potentially enhanced utilization of copper. In a "proof-of-principle" study with one human subject, increased utilization of copper was demonstrated for the liposomal system; the experiment is described in detail in Study 6 below. This shows that 1) the aqueous composition containing sodium-copper-chlorophyllin and penetration-enhancing agents delivers copper to the enzyme tyrosine hydroxylase situated at the base of the epidermis and 2) encapsulation of the copper-pigment complex within a liposome increases the amount of copper delivered.

Another aspect of the present invention is that controlled dissociation of the sodium-copper-chlorophyllin complex is possible, in part because of the high stability of this complex. Normally, inorganic and organic copper salts, including copper-peptides, are not very stable with regard to binding copper. The inherent stability and lack of reactivity of sodium-copper-chlorophyllin is essential for this process to work successfully. We demonstrated the stability of this copper-pigment complex by exposing a sample of the material to intense pulsed light (IPL) flashes in the visible spectral range absorbed by this dye. Stability was monitored by measurement of the dye's full absorbance spectrum, since degradation of the dye would be detectable as changes in the absorbance spectrum. Even after application of ten pulses at the maximum fluence of the flash lamp, the absorbance spectrum of sodium-copper-chlorphyllin remained unchanged, demonstrating high stability for this material.

In nature, many types of botanical pigments protect plants against the free radicals generated from molecular oxygen. Antioxidant pigments are essential for the survival of plants, and the pigments usually contain a metal-ion such as magnesium, zinc, or copper. Although our experiments utilized sodium-copper-chlorophyllin, other examples of botanical pigments containing metals and possessing free radical scavenging properties are considered to be part of this invention. A non-limiting list of examples of such pigments includes carotenoids, chlorophylls, anthocyanins, betalains and phycobilins.

We summarize the invention in greater detail as follows:

In one preferred embodiment of this invention, the carrier vehicle of the copper-pigment complex is a liposomal dispersion, containing lecithin liposomes of very small size, typically between 150-350 nanometers. Bound $Cu^{+2}$ ions are loaded into the liposomes as an aqueous solution of sodium-copper-chlorophyllin. Chlorophyllin itself is a highly effective antioxidant and is expected to neutralize any free radical load put on the skin by reactions between $Cu^{+2}$, hydrogen peroxide, and ultraviolet light.

Copper ions are favored to dissociate from chlorophyllin due to the acidity of the skin compared with the formulated higher pH of the composition. This release process is expectedly slowed by liposome encapsulation. Alternatively, dissociation of the copper-pigment complex can be increased by increasing the skin temperature, for example by optical or sonic heating; or, the release can be slowed by cooling the skin.

Because copper ions bind with many skin peptides and proteins, benefits of this type of topical treatment depend on the applied copper reaching the critical copper-binding sites. Combination of these particular liposomes, characterized by their high stability and small size, loaded with copper bound to a suitable, stable botanical pigment, and delivered within a penetration-enhancing vehicle, are all essential parts of this invention.

In turn, the aims of the present invention are to provide compositions and processes for enhancing cutaneous physiological functions that are, at least in part, dependent on the presence of copper. These copper-dependent functions include repair and growth of connective tissue, regulation of mitochondrial energy metabolism, formation of melanin, and reduction of active oxygen species. The invention discloses the process consisting of:

1) producing a composition containing a non-acidic formulation of copper chemically bound to a botanical pigment possessing antioxidant qualities, the composition thus containing a copper-botanical-antioxidant complex;

2) identification of carrier vehicle containing penetration enhancing agents and encapsulation of the copper-pigment antioxidant complex in stable, submicron liposomes containing relatively high linoleic acid content;

3) locating physiological copper-binding sites in the skin that show signs of chronic skin pathologies or environmental damage;

4) applying topically to the skin the encapsulated copper-botanical-antioxidant complex composition to cause enhanced penetration of the complex to copper binding sites; and, 5) simultaneously delivering skin pH-activated copper ions and plant-based antioxidant pigment to said physiological binding sites to beneficially treat said skin disorders and to protect against further skin damage.

It is disclosed that copper ion ($Cu^{+2}$) that is metallically bound to a botanical pigment, chlorophyllin, can function as a biologically effective copper-delivery system when suitably formulated for topical application. The pigment part of the complex can function as an antioxidant in the skin, thereby reducing inflammatory oxidizing radicals and skin inflammation. The list of copper-dependent enzymes that are normally active in the skin, and thereby affected, includes lysyl oxidase (cross-links collagen fibrils to form the structurally supportive collagen fibers), superoxide dismutase (active in the reduction of damaging oxygen species), tyrosine hydroxylase (important in the synthesis of melanin and the neurotransmitter norepinephrine). Other copper-containing enzymes found in the skin are cytochrome C oxidase (involved in production of the skin's high-energy metabolic substrates) and dopamine beta-hydroxylase (involved in regulation of dopamine and norepinephrine). By explicitly targeting donation of copper to enzymes and copper-dependent wound-healing peptides, via the compositions and processes disclosed in this invention, we imply to cover all copper-dependent needs of the skin.

We have described the importance of copper ions in skin biology, given the necessary presence of copper at catalytic sites of various enzymes, noting also its association with small peptides, such as GHK, which modulate recovery from injury. Whereas botanically-derived pigments such as chlorophylls and carotenoids have been used previously in skin care formulations for their antioxidant potential, binding copper ions with such botanical pigments, specifically to deliver copper, is new. Chlorophyll and chlorophyllin have been used to sanitize and deodorize wounds, to treat burns, blisters, ulcerations, psoriasis, and as additives to hair growth preparations. Copper ions, in bound forms such as copper sulfate, copper glycosides, copper sucralphate and copper gluconate, have had prior use as topical anti-inflammatory agents and in the treatment of spider veins, cellulite, poison ivy, as well as in antiviral compositions. Sodium-copper-chlorophyllin has been previously used as a photomodulation agent: whereby light energy absorbed by this compound, for example from a laser, is transferred to a neighboring, endogenous skin-cell pigment, thereby "energizing" the cell. The copper-pigment may thereby function as a skin or hair growth stimulation agent. However, copper of this form has not been viewed to have an active role, other than stabilizing the molecular structure of chlorophyllin.

Copper-chlorophyllin has been used previously as an internal deodorant in tablet form, in combination with proteolytic enzymes for the debridement and healing of ulcerative wounds and as a colorant in dentifrice, bone cement, and certain dry foods. Oil-soluble copper-chlorophyll and water soluble sodium-copper-chlorophyllin have not been used commercially in pharmaceutical or cosmeceutical skin care products, except for limited use as a deodorant and wound healing additive to products used to treat deep, open wounds such as decubitus ulcers and colostomy openings. The world patent literature does show the potential use of sodium-copper-chlorophyllin as deodorant or disinfectant additive to cosmetic bath cleansers, facial masques, and general purpose moisturizing creams. However, neither copper-chlorophyll nor sodium-copper-chlorophyllin have ever been used commercially in products as topical treatments for chronic dermatoses or any skin disease, for the treatment of photodamaged skin or for the treatment of specific facial cosmetic issues such as enlarged pores, acne scars, or under eye circles, as disclosed in this invention.

It may be assumed that sodium-copper-chlorophyllin has not been used in cosmetic products in any significant way simply because the material is a dark-green pigment, even at low concentrations. For example, sodium-copper-chlorophyllin exhibits a dark-green color in water at 0.1% by weight. Topical use products are typically uncolored or lightly colored with dyes to avoid staining of the skin or with insoluble and non-staining inorganic pigments. Green is, of course, not a natural skin tone. Our studies show that sodium-copper-chlorophyllin within liposomes, or in an aqueous gel vehicle with water soluble penetration enhancers, will penetrate the skin. We disclose here that concentrations up to 0.1% by weight for very light skin and up to 0.5% by weight for very dark skin can be used topically; that is, the pigment is absorbed and is not visibly evident.

The novelty of the present invention is supported by the following facts:

1. Based on history of use, one would not expect a priori that the oil-soluble copper-chlorophyll or the water-soluble copper-chlorophyllin would readily penetrate intact skin or even skin compromised by acne or rosacea;
2. Based on history of use, one would not expect the low level of copper-chlorophyllin, for example, 0.1% by weight—a level used as a colorant in dentifrice and foods, to produce visible improvements in skin condition;
3. Based on history of use, one would not expect visible reductions in pore size, uneven skin coloring, and increased tensile strength of skin after twice daily use of sodium-copper-chlorophyllin for only 2 to 3 weeks;
4. Based on history of use, one would not expect significant antimicrobial activity against the bacterium involved in acne (*P. acnes*) and hence significant anti-acne activity.

These findings are detailed in discussion of experimental studies presented in the next section.

The potential of sodium-copper-chlorophyllin to be a copper-delivery agent, transferring chlorophyllin-bound copper to copper-dependent enzymes in the skin, is new, as is the concept of using the pigment to reduce free radicals produced by the additional free copper load.

We next outline the preparation of one such "therapeutic unit", in an embodiment of the invention that utilizes sodium-copper-chlorophyllin as the copper-pigment complex. Botanical pigments invariably possess a metal-ligand binding site: in natural chlorophyll this binding site is occupied by a magnesium atom. Copper is substituted for magnesium by treating the chlorophyll with an acid, thereby replacing the magnesium with two hydrogen ions (protons). Thereafter, the protons are replaced by a cuprous copper ion ($Cu^{+2}$) by alkaline hydrolysis with a copper salt solution. This process yields oil-soluble copper-chlorophyll. Subsequent alkaline hydrolysis with a sodium salt opens up the cyclopentone ring of chlorophyll and replaces the ester groups with sodium, forming water-soluble sodium-copper-chlorophyllin.

Liposomes loaded with sodium-copper-chlorophyllin were prepared at our request by Rovi Cosmetics (Schluchtern, Germany). Composition (by weight) consisted typically of lecithin (10.00%), sodium-copper-chlorophyllin (5.00%), ethyl alcohol (3.33%), Phenonip (0.50%), and water buffered with potassium dihydrogen phosphate. The pH of the "raw" aqueous liposome dispersion ranged from 7.5 to 8.5. The material was stored in a dark, cool (5° C.) area until used in a treatment composition as detailed below.

Liposomes containing sodium-copper-chlorophyllin can also be prepared by using high linoleic acid lecithin (Phospholipon 80® or Phospholipon 85G®) supplied by American Lecithin Company (Oxford, Conn.) or by Phospholipid GmbH (Cologne, Germany). Typical liposome formulations using Phospholipon lecithin and sodium copper chlorophyllin are detailed below in Exhibit 1 (Formula number JPM-01-03-B; all ingredients percentages are by weight)

EXHIBIT 1

| Sodium Copper Chlorophyllin liposome; Formula # JPM-01-03-B | |
|---|---|
| Ingredient | % w/w |
| Phospholipon 85G (Phospholipid GmbH) | 10.00 |
| Sodium Copper Chlorophyllin, USP* | 5.00 |
| Hydrolite-5 (Symrise, Inc.) | 3.00 |
| Butylene Glycol | 4.00 |
| Phenoxyethanol | 0.30 |
| Deionized Water | 77.70 |

*Supplied by Seltzer Chemical Inc., Carlsbad, CA

The above liposome formula (JPM-01-03-B) is made by first combining and dissolving the butylene glycol, Hydrolite-5 (1,2-pentylene glycol), and phenoxyethanol in the deionized water. This mixture is heated to approximately 50° C. before adding the sodium copper chlorophyllin. This mixture is mixed until the chlorophyllin salt is fully dissolved. The mixture is then cooled to 25-30° C. and the Phospholipon lecithin is added. The aqueous solution of sodium copper chlorophyllin and the lecithin are homogenized with a Waring® type blender, Osterizer®, Eppenbach® or Silverson® homogenizer or a similar mixer capable of high shear mixing. High shear mixing is continued at 3000-5000 rpm for approximately 15 minutes to create a uniform liposome dispersion with the average liposome particle measuring between 150-350 nanometers.

The resulting liposomal dispersion of sodium copper chlorophyllin is a dark green, syrup-like liquid with a pH of between 8.5-9.5. Buffer solution may be added to maintain the pH of the final liposome dispersion between 7.5-8.5.

Liposome dispersions of the sodium copper chlorophyllin can also be made by changing the ratio of Phospholipon from the 2:1 ratio of lecithin:sodium copper chlorophyllin used in Exhibit 1 to higher or lower ratios of Phospholipon to chlorophyllin salt.

In another embodiment of the invention, the raw liposomal dispersion supplied by Rovi Cosmetics GmbH was formulated into a cosmeceutically acceptable gel of the following composition shown below in Exhibit 2 (all components are listed in percentage by weight):

EXHIBIT 2

| CHLOROPHYLLIN TREATMENT GEL; FORMULA #28-145 | |
|---|---|
| Ingredient | % w/w |
| Carbopol 940; 2% dispersion | 55.00 |
| 1,3-Butylene Glycol | 4.00 |
| Ethanol SD 40, 190 Proof | 3.50 |
| Sodium Lactate, 60% (Patlac NAL; RITA) | 1.60 |
| Pentylene Glycol (Hydrolite-5) | 4.00 |
| Phenoxyethanol | 0.75 |
| Sodium Hydroxide solution, 25% | 1.50 |
| Rovisome I chlorophyllin* (Rovi) | 2.00 |
| Deionized Water (add a sufficient amount to make) | 100.00 |

*Rovisome I chlorophyllin is a custom liposomal dispersion containing 5% w/w sodium-copper-chlorophyllin complex in a high linoleic acid lecithin shell.

The final concentration of sodium-copper-chlorophyllin in the above treatment gel is 0.1% w/w. The pH of the gel was typically adjusted to between 7.2-7.6 with NaOH solution and the formula amount shown is increased until a minimum pH of 7.2 is achieved. The formula shown in Exhibit 1 above would be made by first creating a Carbopol® (Noveon Corporation) gel adjusted to a pH of between 7.2-7.6 with sodium hydroxide solution, adding all ingredients other than the Rovisome chlorophyllin liposome and, as a last step, uniformly dispersing the Rovisome chlorophyllin liposome throughout the neutralized gel. Formulas typified by Exhibit 2 have shown to maintain viscosity, pH and uniform dispersion of the sodium copper chlorophyllin liposome through accelerated stability tests that would project to several years of shelf life without significant change.

The topical gel shown in Exhibit 2 has also been formulated by creating submicron (150-350 nanometer) liposomes of sodium-copper-chlorophyllin complex with the use of Phospholipon 85G supplied by American Lecthin Company as previously shown in Exhibit 1. This liposome formula (JPM-01-03-B) was then incorporated in a topical gel with the final formula depicted in Exhibit 3 below (all ingredient percentages are by weight):

EXHIBIT 3

| CHLOROPHYLLIN TREATMENT GEL; FORMULA # JPM-01-35 | |
|---|---|
| Ingredient | % w/w |
| Carbopol 940; 2% dispersion | 55.00 |
| 1,3-Butylene Glycol | 4.00 |
| Sodium Lactate, 60% (Patlac NAL; RITA) | 1.60 |
| Pentylene Glycol (Hydrolite-5) | 4.00 |
| Phenoxyethanol | 0.75 |
| Sodium Hydroxide solution, 25% | 1.50 |
| Sod. Copper Chlorophyllin liposome # JPM-01-03-B* | 2.00 |
| Deionized Water (add a sufficient amount to make) | 100.00 |

*Formula JPM-01-03-B is a liposomal dispersion of 5% w/w sodium-copper-chlorophyllin complex in a high linoleic acid lecithin shell (Phospholipon 85G).

The final concentration of sodium-copper-chlorophyllin in the above treatment gel (Exhibit 3) is 0.1% w/w. The pH of the gel was typically adjusted to between 7.2-7.6 with NaOH solution and the formula amount shown of NaOH solution is increased until a minimum pH of 7.2 is achieved. The formula shown in Exhibit 3 is made by first creating a Carbopol gel adjusted to a pH of between 7.2-7.6 with sodium hydroxide solution, adding all ingredients other than the chlorophyllin liposome and, as a last step, uniformly dispersing the chlorophyllin liposome (JPM-01-03-B) throughout the neutralized gel.

The following studies were conducted to evaluate the effectiveness of such compositions.

Study 1

This study looked at the effects of 0.10% by weight sodium-copper-chlorophyllin, encapsulated within lecithin liposomes and dispersed in an aqueous gel base, on facial redness in rosacea. Digital photos were taken, and spectrophotometric measurements quantified erythema. Color was expressed by the spectrophotometer in "tristimulus" parameters $L^*$, $a^*$, $b^*$, where $L^*$ expresses the "lightness" or brightness of the skin color, $a^*$ expresses the relative redness of the color using a standard green-to-red color space axis, and $b^*$ expresses the "yellowness" of the skin on a standard blue-to-yellow color space axis. The value of $a^*$ is a highly sensitive expression of the degree of erythema. Normal facial skin is measured to have $a^*$-values around 10, whereas erythemic conditions typical of rosacea elevate $a^*$ values to 15, 20, or even higher.

The gel containing 0.10% sodium-copper-chlorophyllin was applied by the patients to their own face twice daily for six weeks. Photographs and colorimetric readings were done at the pre-treatment visit and repeated at 2, 4 and 6 weeks thereafter. The patients did not use any other treatments that would reduce redness. Color measurements were made at each of the four office visits. The measurement sites selected were the forehead, the left and right malar regions (cheeks), the nose, and the chin. Examination of the collected data indicated that colorimeter readings on the chin are characterized by large sampling error, because the contour of the chin can not be reproducibly interfaced with the optical window of the colorimeter. Therefore, readings of chin color were omitted from the analysis. The four remaining facial sites (forehead, both cheeks, and the nose) were not erythemic in all patients, and non-involved sites were also ignored. With these necessary qualifying conditions, a grand total of 24 facial regions, distributed among 7 patients, were identified as significantly elevated in skin redness at the outset and were followed throughout the study.

The redness of these 24 facial regions, measured at weeks 0, 2, 4, and 6 of twice-daily treatment, were fit to a statistical regression line:

$$y=-0.017x+0.969+\text{Error},$$

where "Error" refers to the calculated experimental estimation of $a^*$, y is the fractional skin redness parameter defined as the value of $a^*$ at week x divided by the value $a^*$measured at the pre-treatment visit ($x=0$). Consequently, y has the value 1.0 for the pre-treatment visit, and subsequent values of y represent the fractional value of $a^*$ relative to its value at $x=0$. This regression analysis had a two-tailed probability value 0.0063, which is statistically highly significant, and therefore the −1.7% slope of the linear regression line is a meaningful conclusion from the data. This drop rate amounts roughly to a 10% drop in $a^*$ over the six-week duration of the study, corresponding to a drop in $a^*$ of 1-2 units for these patients: which is a visible improvement.

Study 2

In prior art, U.S. Pat. No. 6,663,559 "Method and apparatus for the photomodulation of living cells", sodium-copper-chlorophyllin is mentioned as a suitable ingredient for light-based therapy of various skin disorders, specifically treatment of the skin with LED arrays. Sodium-copper-chlorophyllin was disclosed therein to enhance the transfer of light energy into the skin, due to the chromophoric nature of chlorophyllin. Physiological benefits obtained from release and subsequent biological uptake of copper and the antioxidant action of chlorophyllin has heretofore not been recognized.

We first investigated the impact of LED-treatment on rosacea, without any copper-pigment complex, and compared the outcome against the improvements found for the copper-pigment complex, described in Study 1. Four rosacea patients were treated twice weekly for two weeks with an LED light source (Gentle Waves light-emitting-diode system using yellow light at a wavelength of 588 nanometers). Linear regression analysis of normalized $a^*$ values, as in Study 1, measured at two time points, week 0 (pre-treatment) and week 2, gave the equation $$y=0.05x+1+\text{Error},$$

with a 2-tailed probability of 0.20: not statistically significant (Although not significant, the regression analysis suggests an average rise, not a decrease in $a^*$ over the two-week LED treatment). For comparison, limiting the analysis of Study 1 data to only the first two weeks of sodium-copper-chlorophyllin treatment, gives the regression line $$y=-0.054x+1+\text{Error},$$

with a 2-tailed probability of 0.0022, showing a statistically significant drop in $a^*$ values of 5.4% on average per week for the first two weeks of treatment with the sodium-copper-chlorophyllin liposome gel composition.

It is therefore arguable that the reduction in skin redness seen in Study 1 is due to biochemical, not optical, properties of sodium-copper-chlorophyllin. Also, these results are not a foregone conclusion from prior art that utilized sodium-copper-chlorophyllin in support of light-based treatment modalities. In fact, our study suggests that the erythemic component of rosacea may at first be aggravated by light exposure, whereas sodium-copper-chlorophyllin without light therapy quickly provides substantial results.

Study 3

A similar study was carried out on skin redness in two rosacea patients, utilizing an intense pulsed light (IPL) source and results were compared against the outcome obtained on the same patients using the same 0.10% sodium-copper-chlorophyllin gel. Regression analysis of changes in the redness parameter $a^*$ of nine IPL-treated facial sites (cheeks), receiving light-treatment at the 6 and 10 week time points, gave the statistical result $$y=1-0.002x+\text{Error},$$

predicting essentially a flat response over the 10-week study, with a two-tailed probability of 0.81: which is not statistically significant. Subsequent treatment of these patients with the sodium-copper-chlorophyllin gel gave the linear regression model $$y=-0.020x+0.989+\text{Error},$$

with a 2-tailed probability of 0.0016, which is highly statistically significant. These results essentially corroborate those found in Study 1 and in Study 2: during the first few weeks of light treatment, the copper-pigment complex reduces the measured value of the skin redness parameter $a^*$ by about 2% per week, whereas the LED and IPL treatments do not yet appear to elicit a significant response.

Study 4

In this clinical trial, an aqueous gel base containing the dispersion of lecithin liposomes and 0.10% by weight sodium-copper-chlorophyllin was evaluated for its effectiveness in treating large pores on the nose and/or cheeks, acne, oiliness of skin, and blotchiness (uneven reddish skin color) of ten subjects with mild to moderate acne. The gel was applied to the nose and cheeks twice daily for four weeks. Skin condition was evaluated by both the patients themselves and by an expert clinical grader. Methods of clinical evaluation included visual examination (counting of acne lesions and enlarged pores, visible skin oiliness and smoothness of skin texture) and measurements of oiliness using Sebutape®, and digital photography. Evaluations were carried out at the start of the study and after four weeks of treatment. Results: After four weeks of treatment most of the ten patients had a decrease in skin oiliness (8/10), most had fewer enlarged pores (9/10), a few had less acne (3/10), less sebaceous thickening of the skin (4/10), and smoother skin (3/10). In their self-assessment, all ten patients felt that their skin condition improved, especially with regard to reduced oiliness, pore size and overall appearance. Sebutape measurements were made at four facial sites: the right side and left side of the forehead, plus the nose and the chin. A global parameter of overall skin oiliness was calculated by summing these four Sebutape measurement values for each patient at the start of the study, and again at two weeks and at four weeks into the treatment. The Sebutape results showed an average 9% reduction in the amount of skin-surface oil after two weeks and an average reduction of 13% at four weeks; the latter is statistically highly significant. It was also noticed that most of the patients had reduced inflammation (redness), particularly one patient with blotchy facial redness. Overall, the study indicated that the treatment results in dramatic reduction of inflammation.

Study 5

This study was conducted at a different clinical research site, and again examined the benefits of a twice-daily facial application of the 0.10% sodium-copper-chlorophyllin gel. Ten subjects, men and women 18-30 years of age, were enrolled in the study. Each subject had mild to moderate acne, with large, visible pores on the nose and/or cheeks, oily skin and blotchy skin coloration. Clinical grading of enlarged facial pores, oiliness and blotchiness were performed during the panelists' initial visit and repeated after three weeks of treatment. Acne was evaluated by counting inflammatory lesions (papules, pustules and nodules) and non-inflammatory lesions (open and closed comedones) for the full face (forehead, left and right cheeks and chin) at the initial visit and after three weeks. The subjects also provided self-assessment diary data of their skin condition throughout the study. Results: The following table summarizes the percentage of statistically significant improvements determined at the three-week time point compared with pre-treatment values, as determined by clinical grading.

| Attribute | Percentage Improvement |
| --- | --- |
| Oiliness | −36.1% |
| Enlarged pores | −21.9% |
| Blotchiness | −26.8% |
| Closed Comedones | −28.3% |
| Global Acne Score | −13.0% |
| Face Overall | −18.6% |

The majority of subjects (8/10) noted various degrees of improvement in their own skin condition, mainly with respect to reduced oiliness, visibility of pores and evenness of color and texture. Digital photographic analysis utilizing the VISIA® clinical grading system calculated significant reduction in pores, acne-related porphyrins, and improvement in overall evenness of skin.

Study 6

A small clinical study was carried out using 5 panelists, to investigate whether sodium-copper-chlorophyllin enhances skin tanning following UV-light irradiation. We were in effect testing whether the gel preparation increases tyrosinase activity by increasing the availability of copper in the skin. The net effect of sodium-copper-chlorophyllin on tanning was somewhat unpredictable, because even if copper stimulates melanogenesis by increasing the activity of tyrosinase, the impact of UV may be reduced, because chlorophyllin is a strong UV absorber (sunscreen) and chlorophyllin is also a strong antioxidant, expected to reduce erythema. We therefore compared the degree of tanning produced by the sodium-copper-chlorophyllin (0.10% by weight) against the tanning produced by an identical preparation of sodium-magnesium-chlorophyllin (0.10% by weight). The magnesium-complex of chlorophyllin corresponds to the actual botanical-derived form of chlorophyll, and has approximately the same UV-absorbance and sunscreen attributes as the copper form. Therefore, any increase in melanin formation by the copper-complex over that for the magnesium-complex would be due to copper.

Five people, 18-65 years of age, participated in the study. All were Fitzpatrick skin type III or IV; that is, all five subjects had substantial tanning capability. The minimal erythemal dose (MED) was determined on the lower back of each subject over the first two days of the study. Thereafter 200 microliters of a treatment gel containing 0.10% by weight of either sodium-copper-chlorophyllin or sodium-magnesium chlorophyllin in a liposomal dispersion as described in Studies 1 and 2 was applied to 1 cm$^2$ sites on the lower back and covered with a semi-occlusive skin patch. The gels were re-applied and patched daily for 5 consecutive days to randomly assigned and coded sites on either side of the lower back. After 5 days, the final patches were removed and the test areas were irradiated with simulated solar light, at dosages of either 1.5 or 2.0 MED. Two untreated sites were also irradiated at 1.5 and 2.0 MED for comparison. The irradiated sites, treated and control, were visually graded for "Darkness" and "Degree of Tanning" at 4 days and 7 days post-irradiation. Darkness scores refer to total skin pigment (hemoglobin and melanin), whereas Tanning scores refer more to melanin. Treated areas of each subject were photographed at 7 days after irradiation using macrophotographic techniques, with and without polarized light. Results: The Darkness ranking (in which the sites are ranked on a scale of 1-6, with 1 being the darkest), resulted in the following average scores:

| Treatment | Average Darkness Score | Std. Dev. |
| --- | --- | --- |
| Untreated | 3.95 | 2.03 |
| Mg-Chlorophyllin | 3.55 | 1.60 |
| Cu-Chlorophyllin | 2.80 | 1.47 |

Given the small sample size, the differences amongst the three types of sites are not statistically significant, but directionally the scores show the copper-chlorophyllin treated sites to be the darkest.

The Degree of Tanning scores proved to be more interesting:

| Treatment | Average Tanning Score | Std. Dev. |
|---|---|---|
| Untreated | 5.55 | 1.48 |
| Mg-Chlorophyllin | 5.25 | 0.98 |
| Cu-Chlorophyllin | 6.15 | 1.84 |

(Degree of Tanning is ranked on a scale: 0 = very light tan and 10 = very deep tan).

This study, although involving only 5 subjects, showed the expected directional differences in the tanning response, in that 1) the magnesium-chlorophyllin treated sites had less tanning than the untreated sites, presumably because of the UV-light absorption and antioxidant protection afforded by chlorophyllin, and 2) the presence of the copper atom gave a substantial boost in the tanning response compared to that seen with Mg-chlorophyllin, presumably showing the copper effect.

A small study, on one subject, was conducted to see whether encapsulation of the sodium-copper-chlorophyllin within the liposome enhanced skin tanning, i.e., increased penetration and bioavailability of copper. The study compared treatment with 0.10% by weight sodium-copper-chlorophyllin in a treatment gel composition similar to Exhibit 2, with and without liposome. Three areas on the back received 1.0 MED simulated solar radiation: one area had received no treatment, one area had been pre-treated with the gel without liposome and the third area was treated with the liposome gel. An expert blinded grader scored the resulting skin tanning at 10 days after irradiation, using the Degree of Tanning scale 0 to 10 (darkest). The control, untreated area showed very little tanning and was given a tanning score of 1-2; the area treated using the gel without liposome was scored as 6.0-6.5; the area treated with the liposome gel was scored as 8. These results suggest copper from the copper-pigment complex applied in a vehicle with penetration-enhancing agents reaches and is picked up by melanocytes, with and without the liposome, but that the liposome enhances penetration beyond that achievable with the penetration enhancers used.

Study 7

The unexpected result that the sodium-copper-chlorophyllin gel used in the above described clinical studies reduced acne-associated inflammation and porphyrins led us to propose that we were observing a copper-mediated antimicrobial effect on *Propionibacterium acnes*. To test this hypothesis, a "kill rate" test against *P. acnes* was conducted at a microbiological testing laboratory. The study compared the antimicrobial properties of the treatment gel containing 0.1% sodium-copper-chlorophyllin against the same gel composition with 0.1% sodium-magnesium-chlorophyllin. Antimicrobial activity of the two gels was determined using the standard methodology of counting the number of organisms on test plates covered with the respective gels after 1 hour and 24 hours of incubation. The kill rate is calculated as the logarithmic reduction in the concentration of organisms when compared with the concentration of organisms in the original inoculation material. Results are summarized in the following table:

| Treatment Gel with 0.1% w/w Sodium Copper Chlorophyllin | | | |
|---|---|---|---|
| Organism | Inoculum Level | Average | Log Reduction |
| P. acnes 1 hour | $2.95 \times 10^5$ | No Growth | 5.47 |
| P. acnes 24 hours | $2.95 \times 10^5$ | No Growth | 5.47 |

| Treatment Gel with 0.1% w/w Sodium Magnesium Chlorophyllin | | | |
|---|---|---|---|
| Organism | Inoculum Level | Average | Log Reduction |
| P. acnes 1 hour | $2.95 \times 10^5$ | 6,500 | 1.66 |
| P. acnes 24 hours | $2.95 \times 10^5$ | 2,000 | 2.17 |

A log reduction of 1.66 or 2.17 obtained with the sodium-magnesium-chlorophyllin gel at one hour and 24 hours, respectively, is considered ineffective antimicrobial activity, and may in fact be due to just the gel base itself. On the other hand, the total kill of *P. acnes* seen with sodium-copper-chlorophyllin gel at both incubation times suggests very strongly that the copper exerts significant antimicrobial activity, and we propose it is the copper that dissociates from chlorophyllin that is responsible for the reduction of acne symptoms seen in the clinical studies. The treatment gel vehicle used in the above studies was identical to the formula shown in

What is claimed is:

1. A monomodal method for treating erythematotelangiectatic rosacea, the method consisting essentially of the step of: administering to and leaving on an area of human skin presenting with erythematotelangiectatic rosacea a topically-applied composition comprising consisting essentially of either or both of copper chlorophyllin and sodium copper chlorophyllin in an aqueous solution, the copper chlorophyllin and/or sodium copper chlorophyllin being present in a concentration non-staining to human skin and between 0.0001 and 0.5% by weight of the composition, the aqueous solution contained within liposomes, the liposomes having a lecithin shell having a fatty acid component, more than 50 wt-% of the fatty acid component being linoleic acid, the liposomes having an average diameter between 150 to 350 nanometers, and wherein the liposomes are dispersed in a dermatologically-acceptable carrier and further wherein the topically-applied composition is administered at least once daily for a period of at least two weeks.

2. The method of claim 1 wherein the dermatologically-acceptable carrier contains a skin penetration enhancing ingredient.

3. The method of claim 2 wherein the skin penetration enhancing ingredient is selected from the group consisting of propylene glycol, butylene glycol, pentylene glycol, isopentyl glycol, ethoxydiglycol, dimethyl isosorbide, acetamide MEA, tetrahydropiperine, PEG glyceryl ethers, Levomenol, N-methyl-2-pyrrolidone, dimethyl sulfoxide and methyl sulfone.

* * * * *